United States Patent [19]

Schatz et al.

[11] Patent Number: 4,771,162
[45] Date of Patent: Sep. 13, 1988

[54] APPARATUS FOR TREATING PLASTIC PARTS FOR USE IN DENTAL AND ORTHODONTIC APPLICATIONS

[75] Inventors: Rolf Schatz, Oberndorf/Boll; Bernhard Link, Oberndorf; Emil Nagel, Bad Säckingen, all of Fed. Rep. of Germany

[73] Assignee: FKB Feinwerktechnik und Kunststoffverarbeitungs GmbH, Fed. Rep. of Germany

[21] Appl. No.: 941,618

[22] Filed: Dec. 15, 1986

[30] Foreign Application Priority Data

Dec. 18, 1985 [DE] Fed. Rep. of Germany ....... 3544750

[51] Int. Cl.$^4$ .................................................. F27B 5/04
[52] U.S. Cl. .................................. 219/400; 126/21 A; 219/440
[58] Field of Search ............... 219/400, 405, 354, 440, 219/411, 377, 390, 401; 126/21 A, 21 R; 34/195, 196, 197, 202, 218, 219, 224, 225, 232, 233, 235

[56] References Cited

U.S. PATENT DOCUMENTS

| | | | |
|---|---|---|---|
| 1,721,840 | 7/1929 | Smith | 34/219 |
| 1,986,088 | 1/1935 | Wild | 219/400 |
| 2,093,334 | 9/1937 | Meitzler | 219/400 |
| 2,523,787 | 9/1950 | Spooner | 219/377 |
| 3,288,129 | 11/1966 | Fox | 126/21 A |
| 4,374,319 | 2/1983 | Guibert | 219/411 |
| 4,477,706 | 10/1984 | Mittelsteadt | 219/400 |

FOREIGN PATENT DOCUMENTS

| | | | |
|---|---|---|---|
| 2021194 | 4/1970 | Fed. Rep. of Germany . | |
| 623941 | 7/1961 | Canada | 34/202 |
| 168880 | 4/1934 | Switzerland | 219/400 |

OTHER PUBLICATIONS

DeTrey, Biopol Pressure-Cure Apparatus.

*Primary Examiner*—E. A. Goldberg
*Assistant Examiner*—Teresa J. Walberg
*Attorney, Agent, or Firm*—McGlew & Tuttle

[57] ABSTRACT

A device for treating plastic parts for use in dental and orthodontic applications includes a pressure receptacle which has walls which define a hollow interior with an opening which is closable by a cover or lid. A support for material to be treated is placed within the hollow interior at a spaced location in the interior walls and adjacent a heating device which is advantageously an electric heating element. The device includes a rotatable fan which is advantageously mounted on the vessel as a shaft which extends through the vessel interior and carries a rotatable fan which is rotated so as to direct a gas such as air past objects held on a support and past the heater which maintains the circulating gases at a temperature which permits polymerization of the parts. The heating air is continuously circulated and it is heated by the heater sufficiently to maintain a selected polymerization temperature.

12 Claims, 2 Drawing Sheets

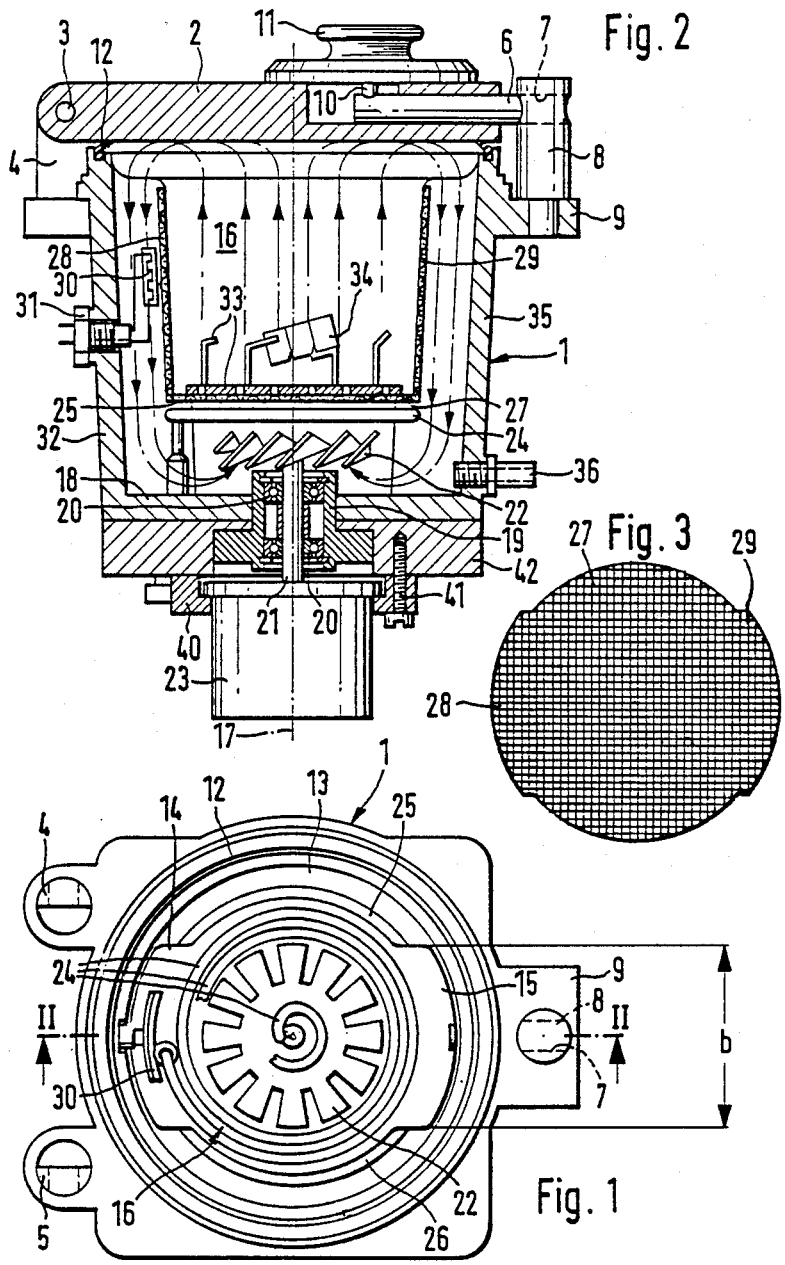

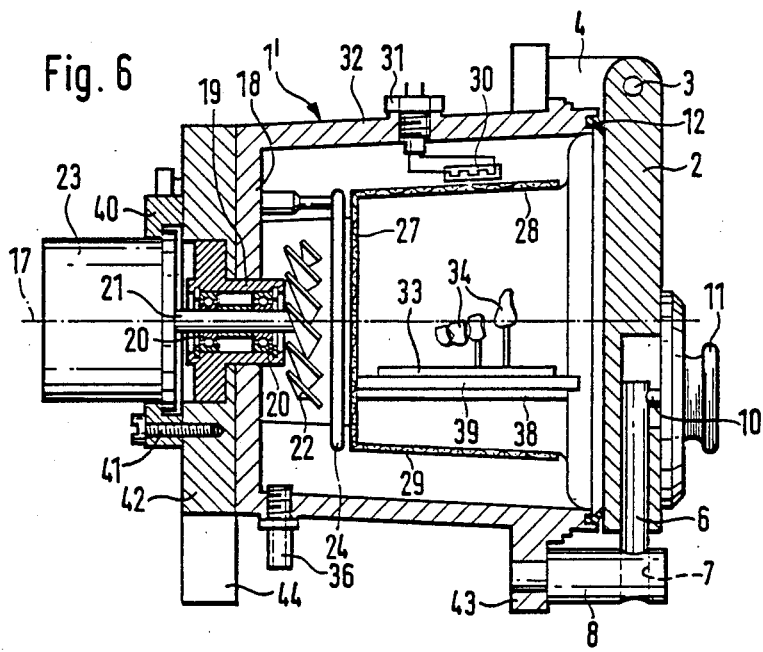
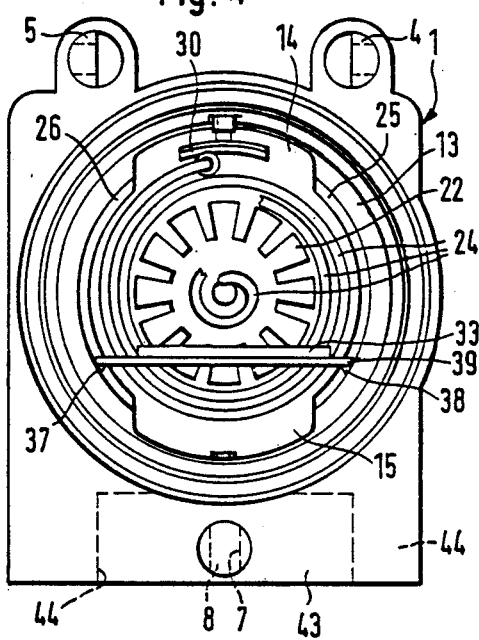
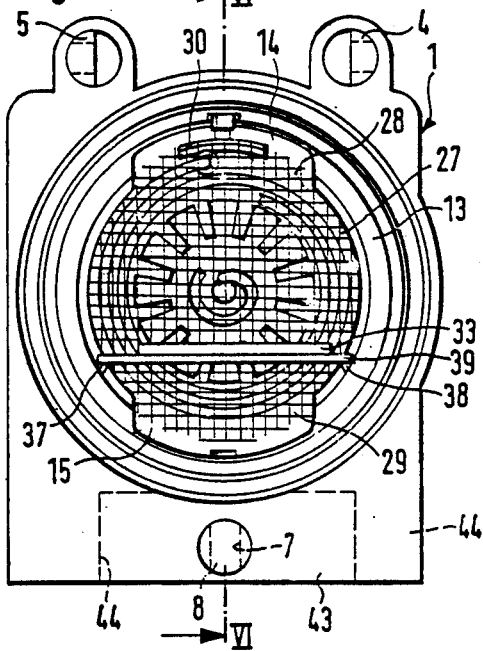

APPARATUS FOR TREATING PLASTIC PARTS FOR USE IN DENTAL AND ORTHODONTIC APPLICATIONS

FIELD AND BACKGROUND OF THE INVENTION

This invention relates in general to orthodontic and dental devices and in particular to a new and useful method and apparatus for treating by thermal polymerization plastic elements which are used for dental purposes.

The invention relates particularly to a process and a device for thermal polymerization of plastics for dental purposes in an enclosed space of a pressure receptacle in which a heated medium enclosing the material to be polymerized is placed under excess pressure.

The pressure polymerization equipment currently used in the dental laboratory to make dental prosthetics are only suitable for polymerization processes that take place in a liquid medium such as water or glycerin, heated to a polymerization temperature of 120° C., for example, and simultaneously put under pressure of 6 bar, for example. In the water polymerization process, for each new polymerization procedure the pressure receptacle of the polymerization equipment is usually filled with fresh, cold water in which the material to be polymerized must be completely immersed. With the polymerizates used in such cases, the major factors in obtaining a good result from the polymerization are to maintain the polymerization temperature at exactly the right level and further to make sure that the temperature is evenly distributed throughout the cavity of the pressure receptacle. These requirements can be met easily and thoroughly with water as the medium in which polymerization takes place, because water is a good conductor of heat. On the other hand, however, the use of water as the polymerization medium entails the disadvantage that a relatively large amount of heat energy is required to heat it up to a specific polymerization temperature. Furthermore, it is somewhat tedious to handle in that for the each new polymerization procedure the pressure receptacle has to be refilled with water and then drained again afterwards. Moreover, the use of water as the polymerization medium presupposes a pressure receptacle that can only be opened from the top.

To accomplish slow heating and cooling of the plastic and hence avoid stresses in the molded bodies that have walls of varying thicknesses, a prior art process (German Patent Disclosure No. 2,021,194) of the general type discussed above provides that the molded bodies are brought into contact with the surrounding contact fluid while the fluid is still at a temperature below the polymerization temperature. The molded bodies are then heated together with the contact fluid up to a polymerization temperature and finally cooled slowly. For this purpose, an additional receptacle is provided that is equipped with a heat condenser that is placed in an influx channel placed into the interior space of the receptacle or an influx channel is provided in the interior space of the receptacle.

Apart from the fact that the contact medium used is still a liquid that has to be changed often, an additional receptacle is required to hold the material to be polymerized, which makes the device more expensive and handling is more involved.

In another polymerization process, a predetermined amount of water is put into a heatable pressure receptacle with the material to be polymerized and heated to a vapor after the pressure receptacle is closed. What results is a mixture of hot air and water vapor. This process has not been found to be particularly good in practice, because uneven hardening with uneven degrees of hardness and uneven coloring have been noted. Furthermore, with this process, to an even greater degree than with the polymerization in a water bath, problems at the interface between metal and plastic due to the formation of gaps have been noted. Obviously, with this process, the transfer of heat from the heat source to the material to be polymerized is inadequate.

Recently a device has appeared on the market in the U.S. (Justi Pakto, H. D. Justi Company, Oxnad, CA) consisting of a sort of pressure cooker with a lid and equipped with a gas supply line, manometer, thermometer and a pressure satety valve. The pressure range that can be obtained is between 1.4 and 2.7 bar. The temperature range is between 120° and 204° C. and is achieved by means of a built-in 5-step electric hot plate. Because of the low pressure obtainable, only a single plastic material can be used in this equipment, namely 100% polyglycoldimethacrylate. That material, however, is not comparable in quality with the filled or unfilled plastics more commonly used today for dental work that are improved in wear resistance, impact strength, hardness, color and so forth and come very close to the properties of natural teeth. They do require, however, very process polymerization conditions to be maintained.

SUMMARY OF THE INVENTION

The invention provides a process and a device for performing the process that avoid the present disadvantages and allow for shorter heating up times and less energy consumption.

In accordance with the invention air, or an inert gas, is used as the heated medium and it is forcibly circulated in an enclosed space of a pressure receptacle so that is passes a controlled heated device and the material to be polymerized.

Aside from the fact that water is no longer required, this process offers the advantage to the dental laboratory that considerably less heat energy is required to heat the gaseous medium in the enclosed space of the pressure receptacle, and that nonetheless the temperature required for polymerization can be obtained sufficiently precisely and sufficiently evenly in the interior space of the pressure receptacle and the temperature is maintainable throughout the length of the polymerization process, which can take several minutes. The medium can be heated up to the desired polymerization temperature in a considerably shorter time than is possible with the same heat output when water is used as the polymerization medium.

For the inert gas, the primary choices are nitrogen and carbon dioxide. However, helium or argon could be used, as well.

Particularly good results, especially in the dental field, can be achieved when the heating time for the mixture is shorter than two minutes, and in particular shoter than one minute.

After the heating phase, the temperature should not fall by more than 5° C., and preferably not by more than 2° C., inside the cavity of the pressure receptacle.

For dental purposes, the pressure should be at least 4 bar, preferably between 5 and 10 bar. At pressures lower than that, conventional filled or unfilled plastics for dental work, which are suitable for the process, when heated to a polymerization temperature between 90° and 140° C., may partially vaporize and thereby create problem bubbles and foam.

The invention provides a device for performing the process pursuant of a pressure receptacle that can be sealed shut by means of a lid or door and is equipped with a built-in heating device to heat the medium, controllable by means of a temperature sensor. The device includes a pressurized air or pressurized gas connection and within the interior space of the pressure receptacle the temperature that must be achieved and maintained for purposes of the polyaerization process in the gaseous medium surrounding the material to be polymerized is reached in the shortest possible time. The temperature is maintained as precisely as possible over the entire polymerization time, and is evenly distributed over the entire surface of the material to be polymerized.

The inventive device includes a fan wheel driven by an electric motor that creates a flow of air or gas in the pressure vessel taht is directed through a heating device situated on one plane onto the maerial to be polymerized.

This arrangement not only provides for the continuous, even circulation of the medium within the pressure receptacle, but also insures that during the entire polymerization process there is always enough heat energy at the desired temperature being supplied to the material to be polymerized and the heating fluid is available to maintain the polymerization process throughout the expected polymerization time.

An embodiment of the invention is advantageous in that an axial fan wheel is positioned inside the pressure receptacle at the spot where it is least in the way and furthermore is most effective in directly conveying the heat produced by the heating device to the material to be polymerized.

An embodiment of the invention substantially improves heat distribution over the entire cross-section of the interior of the pressure receptacle and at the same time evens out the flow of air or gas produced by rotation of a fan wheel.

An embodiment of the invention is advantageous in the arrangement of the heating device and a fan wheel, so that it is the least obstructive and is easily mounted and most readily accommodated in spatial terms. In the case of equipment in which the loading opening is not on top but in the front, the arrangement offers the additional advantage that the bearing surface on which the object holder with the material to be polymerized is placed runs not parallel but perpendicular to the plant of the spiral heating element and thus presents the least resistance to the flow produced by the fan wheel.

Other embodiments of the invention improve flow conditions inside the enclosed polymerization space, or further improve these flow conditions and also make for better heat distribution inside the entire polymerization space in the pressure receptacle.

The positioning of the temperature is such that it not only insures precise detection of the temperature prevailing in the entire polymerization space, but also protects the temperature sensor against outside influences, and a particular arrangement of the pressurized air or pressurized gas connection insures that the pressurized medium fed in is first conveyed to the heating spiral, is there heated and then distributed in the flow produced by the fan wheel. Still another possible arrangement of the fan wheel and design of the pressure receptacle insures even temperature distribution inside the pressure receptacle, and another offers the possibility of usng the same pressure receptacle to perform polymerization by radiation, in which thanks to the mirror effect of the fan wheel the radiation is also reflected onto the surfaces of the material to be polymerized that face away from the radiation source. By maintaining a given pre-heating temperature in the pressure receptacle, the heat-up time to the requisite polmerization temperature can be substantially shortened.

Accordingly it is an object of the invention to provide an improved device for treating plastic parts for use in dental and orthodontic applications which comprise a pressure receptacle which has an inner wall defining a hollow interior which is openable at an end or a top thereof and is closed by a cover and which includes a support in the vessel for material to be treated which is spaced from the interior walls and from a heating device arranged within the hollow interior and which includes means for circulating a gas past the heating device and to the material on the support.

A further object of the invention is to provide a process for the thermal polymerization of plastics for dental purposes and orthodontic purposes which includes a hollow pressure vessel which has a support for the objects and which comprises placing the material in the vessel on the support, heating the interior of the vessel and directing a heating gas over the heater and over the objects to be treated and heating the gases to maintain a selected temperature.

A further object of the invention is to provide a device for treating plastic parts which is simple in design, rugged in construction and economicl to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings

FIG. 1 is a top plan view of a pressure receptacle of a polymerization device with the lid removed constructed in accordance with the invention;

FIG. 2 is a sectional view taken along line II—II of FIG. 1;

FIG. 3 is a top view of a screen-like insert;

FIG. 4 is a view similar to FIG. 1 of another embodiment of the pressure receptacle of a polymerization device with the closing element removed and without the screen-like insert;

FIG. 5 is a view similar to FIG. 4 with the screen insert in; and

FIG. 6 is a sectional view through line VI—VI in FIG. 5 showing the vessel in a horizontal position.

DESCRIPTION OF THE PREFERRED EMBODIMENTS

Referring to the drawings in particular, the invention embodied therein comprises a device for treating plastic parts for use in dental and orthodontic applications, and particularly for effecting the polymerization of plastic elements for dental purposes, which includes a pressure receptacle or vessel 1 having a support 33 therein which is spaced from the interior walls of the vessel and provides a means for supporting articles to be treated therein at a spaced location from the heating device 24. The invention includes means for heating the gases such as air which is in the vessel including a heating element 24 which comprises an electrical resistance heater which is connected to means for regulating its temperature and hence the temperature of the gases in the chamber which may, for example be connected to respond to a circuit connected to a connector 31 having a temperature sensor 30. The gas such as air is circulated over the articles 34 which are held on the support 33 and the temperature is controlled so as to achieve a desired polymerization of the plastic articles.

The pressure receptacle 1 shown in FIGS. 1 and 2 is essentially shaped like a circular pot that tapers slightly toward its end or bottom. Its top opening is closable by means of a lid 2 that is pivotally mounted by means of a bearing shaft 3 on hinge pins 4 and 5. In closed position as shown in FIG. 2, the lid 2 can be locked by means of a locking bolt 6 that can be slid into a horizontal hole 7 of a locking peg 8 that is fastened standing upright in an eye lug 9. By means of a cross-pin 10 the locking bolt 6 is connected with a manually operable slide 11. The circular top of the pressure receptacle 1 is equipped with a circular sealing lip 12, which lies tight against the underside of the lid 2. The pressure receptacle is formed as one piece by die-casting and has relatively thick walls 13 in which are wrought two diametrically opposite niche-like extensions 14 and 15 with a width b equal to approximately half the average inner diameter of the pressure receptacle 1. The significance of these niche-like extensions 14 and 15 that run the entire height of the interior space 16 will be explained in greater detail below.

Concentric to the vertical axis of symmetry 17 of the pressure receptacle 1 and in the floor 18 thereof the shaft 21 of an axial fan wheel 22 is turnably mounted by means of a bushing 19 and ball bearings 20 placed therein, the fan wheel 22 being driven by an electric motor 23 and thereby producing a flow moving from botton to top in the center of the interior space 16 and from top to bottom in the niche-like extensions. The electric motor 23 is attached by means of a flange ring 40 and screws 41 to a base plate or floor 42, which is in turn screwed into a floor 42. Directly above the axial fan wheel 22 is positioned a heating device 24 in the form of an electric spiral heating element whose spiral coils are arranged on a plane parallel to the plane of rotation of the axial fan wheel 22 with very small radial intervals between them. The vertical or axial distance of the axial fan wheel 22 from the inner surface of the floor 18 is less than its distance from the heating device 24, but designed large enough that the axial fan wheel can produce a sufficient axial suction effect.

Directly above the heating device 24 is a baffle plate or screen 27 comprising a fine-mesh metal wire screen that covers the entire cross-sectional surface of the heating device 24 and rests on two bearing surfaces 25 and 26 in the shape of segments of a circle positioned on either side of niche-like extensions 14 and 15 in a plane parallel to the floor 18. In addition, the baffle plate 27 is provided with lateral, diametrically opposed, arc-shaped projecting wall elements 28 and 29 that fit into the niche-like extensions 14 and 15 and separate them from the rest of the interior space 16. The wall elements 28 and 29 also comprise a fine mesh wire screen similar to the baffle plate or screen 27 and are formed as one piece there with the latter. As FIG. 2 shows, these wall elements 28 and 29 do not extend axially all the way up to the inside surface of the lid 2; instead, they end at a distance from the inside surface of the lid 2 that is equal to the radial depth of the extensions 14 or 15, so that the flow hitting said inside surface, divided roughly in two, is free to pass into the niche-like extensions 14 and 15 and there is able to continue on down. In the extension 14, about half-way up from the heating device 24, there is a small temperature sensor plate 30 whose electrical connecting lines are connected with a connecting bushing 31 screwed tightly into the wall section 32 of the niche-like extension 14. The temperature sensor plate 30 is hooked up with an electrical temperature control and regulation device with the aid of which the desired polymerization temperature can be reached and regulated. Such control and regulation devices are part of the state of the art in themselves and therefore require no further explanation here.

The baffle plate 27 resting on the bearing surfaces 25 and 26 serves in turn as a bearing surface for object holders 33 on which artificial teeth, crowns or the like, for example, can be mounted. Object holders of this kind generally consist of perforated discs or wire loops that are placed unattached on the baffle plate 27 and furthermore so designed that they get in the way as little as possible of the flow of air or gas heated by the heating device 24 and penetrating the perforated, fine-mesh baffle plate 27.

In the thinner section of wall 35 in the niche-like extension 15 a pipe connection fitting 36 is provided on a plane that lies beneath the axial fan wheel 22 for hooking up a source of pressurized gas or pressurized air. This arrangement of the pipe connection fitting 36 is designed so that the cold pressurized air or cold pressurized gas introduced into the pressure receptacle 1 through it immediately enters the suction range of the axial fan wheel 22 and is heated before it comes in contact with the material to be polymerized 34.

The device described above, designed for performing thermal polymerization procedures, particularly for dental purposes, works in the following manner:

After the material to be polymerized, which may, for example, be in the form of artificial teeth 34 or crowns, is positioned with the aid of the object holder 33 placed on the baffle plate 27 and the lid 2 is closed and locked, the pressurized air supply or pressurized gas supply and the heating device 24 and fan motor 23 are switched on together with an electrical control device, e.g. connected at 3 as part of the accessory equipment of the polymerization device.

When the predetermined pressure of, for example, 6 bar has been reached inside the pressure receptacle, the supply of further pressurized air or gas is shut off, while the heating device 24 stays on until the temperature sensor 30 registers the pre-set polymerization temperature and takes over control of the heating device 24 from then on in order to keep the temperature at precisely the set level throughout the time required for polymerization. With the aid of the fan motor 23, which is on the entire length of the polymerization process, the axial fan wheel 22 it drives produces a circulating flow of air or gas inside the enclosed pressure receptacle 1 that essentially follows the direction shown in in FIG. 2 by lines with arrows, that is, the flow of gas or air produced by the fan wheel 22, after passing through the coils of the heating device 24, first reaches the baffle plate 27, which acts as a throttling element and heat distributor, where, thanks to the latter's fine mesh openings it is distributed quite evenly over the entire cross-section, rises further and flows around the material to be polymerized 34, subsequently bounces off or is deflected by the underside of the lid 2, thereupon begins to flow in the opposite direction through the niche-like extensions 14 and 15, and finally ends up once again in the suction range of the axial fan wheel 22, ready to begin the circuit over again. In this process, the baffle plate 27 and the wall elements 28 and 29 on its sides act not only as flow guide elements but simultaneously as heat distributors as well, and they help to bring it about that in the entire interior space 16 and in the niche-like extensions 14 and 15 the same temperature and even the same pressure prevails at every point, so that with just one temperature sensor 30 it is possible to detect temperature accurately and control temperature sufficiently precisely for even polymerization.

The embodiment shown in FIGS. 4 through 6 differs from that in FIGS. 1 and 2 only in terms of its operating position. While the pressure receptacle 1 shown in FIGS.1 and 2 has an operating position in which its axis of symmetry 17 is vertical, the pressure receptacle 1' shown in FIGS. 4 through 6 is so designed that its axis of symmetry 17 is horizontal in operating position, and the lid 2 is operated in the manner of a flap. Instead of that, it would also be possible to place the hinge pins 4 and 5 and the joint shaft 3 so that the axis of pivot would be vertical, and the lid 2 could be opened and closed like a door. In order to be able to be used in any operating position, the pressure receptacle 1' can be built into a housing possessing other components and/or, as shown in FIGS. 4 through 6, be equipped with standing strips 43 and standing feet 44.

Another difference with regard to the emobdiment in FIGS. 1 and 2 is that baffle plate 27, which is also found here but is situated on a vertical plane, does not serve as a bearing surface. Instead, a bearing plate 39 is provided which rests on support ribs 37 and 38 and runs perpendicular to the plane of the baffle plate 27 . Object holders 33 are positioned on the plate 39 in the manner shown in FIG. 6. This arrangement has the advantage that the object holder 33 offers considerably less resistance to the flow of gas or air than is the case with the arrangement shown in FIG.2.

All other arrangements and functions are the same as with the embodiment in FIGS. 1 and 2, so that the description given in connection therewith applies here as well.

It is also possible, of course, to provide for a receptacle with a cylindrical or elliptical interior space and to equip it in analogous fashion with an axial fan wheel. In such case, however, the fan wheel could also be placed so that the direction of flow would be perpendicular to the axis of the cylinder or to the axis of symmetry of the elliptical cavity. It can also be helpful to place perforated wall elements within the interior space on three sides as flow guide elements and heat distributors at a certain distance from the side walls to allow flow cycles to be created that this arrangement of wall elements favors.

It is also helpful to provide a pre-heating thermostat switch by means of which the inner temperature of the pressure receptacle can be kept at a constant pre-heating temperature of 80° C., for example, so that the heat-up time required to reach the higher polymerization temperature of, say 120° C. can be shortened.

It is also possible to place a source of radiation suitable for radiation polymerization, such as an ultraviolet source, on the inner side of lid 2 opposite the axial fan wheel, for example, and at the same time to make the surfaces of the axial fan wheel facing back towards the radiation source into mirrors, so that the polymerization radiation is also reflected onto the surfaces of the material to be polymerized that face away fromt he source of radiation.

While specific embodiments of the invention have been shown and described in detail to illustrate the application of the principles of the invention, it will be understood that the invention may be embodied otherwise without departing from such principles.

What is claimed is:

1. A device for treating plastic material for use in dental and orthodontic applications, comprising: a pressure receptacle having walls defining a hollow interior with an opening, said hollow interior being essentially cylindrical having two diametrically opposite niches each having a radial depth; a cover closing said opening, a support for material to be treated positioned in said hollow interior spaced from said walls; a heating device in said hollow interior spaced from said support, said heating device including an electric element heater disposed adjacent said niches, said electric heater element being positioned adjacent an inner wall of said vessel opposite to said cover; means for circulating a gas past said heating device and past said support for material to be treated including an axial fan wheel spaced from said hollow interior of said vessel; a screen-like wall element supported on said niches; and, a baffle plate covering said heating device, said screen-like wall element being spaced from said cover by an amount approximately equal to the radial depth of said opposite niches.

2. A device according to claim 1, including a temperature sensor having a sensor element extending into the interior of said pressure vessel.

3. A device according to claim 2, including a gas connection into the interior of said vessel, a pressurized gas supply connected to said gas connection, said pressurized connection being on the suction side of the fan wheel.

4. A device according to claim 3, wherein said axial fan wheel is positioned in a lower portion of said pressure vessel said fan wheel having a vertical blowing direction.

5. A device according to claim 1, wherein in the vicinity of and inside wall of said pressure vessel opposite to said fan wheel on an outflow side a source of radiation is positioned providing a polymerization radiation including an ultraviolet radiation and wherein the surface of said fan facing the radiation surface is made into mirrors.

6. A device according to claim 5, wherein a preheating thermostat switching device is provided by means of which the temperature of the interior space of said pressure vessel is kept at a constant preheating temperature of approximately 80° C.

7. An apparatus for polymerizing plastic material for dental purposes, comprising: a pressure vessel having walls with interior surfaces defining a hollow interior with a central opening, said vessel including a bottom end wall and a top cover closing said opening; a temperature sensor positioned with said hollow interior; a heating device positioned within said hollow interior; compressed gas inlet means for supplying gas to said hollow interior; a motor-driven blower positioned in said pressure vessel having a central axis for rotation substantially coaxial with a central axis of said pressure vessel, said blower being positioned adjacent said bottom wall; a support for material to be treated positioned in said hollow interior spaced from said bottom wall, said blower being positioned between said bottom wall and said support, said heating device being disposed in a plane substantially parallel to said bottom wall lying between said support and said blower; a screen baffle disk permeable to flow positioned between said support and said heating device covering said heating device over its entire area, a gas stream created by said blower passing through said heater and through said screen baffle disk and past said support for material to be treated.

8. An apparatus according to claim 7, wherein: said blower is spaced from said bottom wall an axial distance at least equal to an axial distance between said blower and said heating device.

9. An apparatus according to claim 7, wherein: said walls forming a hollow interior of said pressure vessel are formed substantially cylindrical with two niche-type enlargements each having a radial depth and having positioned diametrically opposite each other.

10. An apparatus according to claim 9, wherein: each niche-type enlargement is partially covered by a screen baffle wall element, each screen baffle wall element extending from said screen baffle disk covering the heater to a distance spaced from said cover approximately equal to a radial depth of said nich-type enlargements.

11. An apparatus according to claim 10, wherein: said temperature sensor is positioned within one of said niche-type enlargements.

12. An apparatus for polymerizing plastic material for dental purposes, comprising: a pressure vessel having walls with interior surfaces defining a hollow interior with a central opening, said vessel including a bottom end wall and a top cover closing said opening; a temperature sensor positioned within said hollow interior; a heating device positioned within said hollow interior; compressed gas inlet means for supplying gas to said hollow interior; a motor-driven blower positioned in said pressure vessel having a central axis for rotation substantially coaxial with a central axis of said pressure vessel, said blower being positioned adjacent said bottom wall; a support for material to be treated positioned in said hollow interior spaced from said bottom wall, said blower being positioned between said bottom wall and said support, said heating device being disposed in a plane substantially parallel to said bottom wall lying between said support and said blower; a screen baffle disk permeable to flow positioned between said support and said heating device covering said heating device over its entire area, a gas stream created by said blower passing through said heater and through said screen baffle disk and past said support for material to be treated, said walls forming a hollow interior of said pressure vessel are formed substantially cylindrical with two niche-type enlargements each having a radial depth, each niche-type enlargement being positioned diametrically opposite each other, each niche-type enlargement is partially covered by a screen baffle wall element, each screen baffle wall element extending from said screen baffle disk covering the heater to a distance spaced from said cover approximately equal to a radial depth of said niche-type enlargements.

* * * * *

UNITED STATES PATENT OFFICE
CERTIFICATE OF CORRECTION

Patent No. 4,771,162          Dated September 13, 1988

Inventor(s) Schatz et al

It is certified that error appears in the above-identified patent and that said Letters Patent are hereby corrected as shown below:

On the title page:
The name of the second assignee should read

-- Vita Zahnfabrik H. Rauter GmbH & Co. KG  --.

Signed and Sealed this

Fourteenth Day of March, 1989

Attest:

DONALD J. QUIGG

Attesting Officer

Commissioner of Patents and Trademarks